United States Patent
Faulkner et al.

(10) Patent No.: US 6,300,371 B1
(45) Date of Patent: Oct. 9, 2001

(54) RAMESWARALIDE AND RAMESWARALIDE DERIVATIVES

(75) Inventors: D. John Faulkner, La Jolla, CA (US); Y. Venkateswarlu, Hyderabad (IN); K. V. Raghavan, Hyderabad (IN); J. S. Yadav, Hyderabad (IN)

(73) Assignees: Indian Institute of Chemical Technology, Hydrabad (IN); University of California, Oakland, CA (US)

( * ) Notice: Subject to any disclaimer, the term of this patent is extended or adjusted under 35 U.S.C. 154(b) by 0 days.

(21) Appl. No.: 09/293,734

(22) Filed: Apr. 16, 1999

Related U.S. Application Data

(60) Provisional application No. 60/107,461, filed on Nov. 5, 1998.

(51) Int. Cl.[7] .................. A61K 31/19; A61K 31/335; C07D 407/00; C07D 321/00
(52) U.S. Cl. .................. 514/468; 514/450; 549/298; 549/348
(58) Field of Search .................. 514/468, 450; 549/298, 348

(56) References Cited

U.S. PATENT DOCUMENTS

| 4,906,794 | 3/1990 | Umezu et al. | 568/821 |
| 5,276,217 | 1/1994 | Tius | 568/821 |

OTHER PUBLICATIONS

Chan et al., "The Structure of Crotofolin A, a Diterpene with a New Skeleton", J. Am. Chem. Soc. vol. 97, No. 15, pp. 4437–4439.*

P. Ramesh et al., "Rameswaralide, A Novel Diterpenoid from the Soft Coral *Sinularia dissecta*" Tetrahedron Letters 39 (1998) 8217–8220.

Eisch, J.J., et al., The structure of Crotofolin A, a Diterpene with a New Skeleton, J. Am. Chem. Soc. vol. 97, No. 15 pp. 4437–4439.

* cited by examiner

*Primary Examiner*—Alan L. Rotman
*Assistant Examiner*—Binta Robinson
(74) *Attorney, Agent, or Firm*—Fish & Richardson P.C.

(57) ABSTRACT

A diterpene derivative compound, having the formula I, II, or III, compositions, and therapeutic compositions containing the compounds are disclosed. Also disclosed are methods for treating an inflammatory disorder by providing an inflammatory inhibiting amount of the compound as well as methods for obtaining the compound.

22 Claims, 2 Drawing Sheets

$^1H$ (300 MHz, CDCl$_3$) and $^{13}C$ (100 MHz, CDCl$_3$) NMR data for rameswaralide (4) and dihydrorameswaralide (5).

| C# | rameswaralide (4) | | | | dihydrorameswaralide (5) | | | |
|---|---|---|---|---|---|---|---|---|
| | $\delta_C$ | $\delta_H$ | mult., J(Hz) | HMBC | NOESY | $\delta_C$ | $\delta_H$ | mult., J(Hz) | NOESY |
| 1 | 41.7 | 2.58 | m | C2, C14, C15, C16, C17 | H2, H13, H16a, H17 | 39.1 | 2.38 | dt, 13, 3.5 | H2, H13, H16a, H17 |
| 2 | 34.2 | 2.39 | dd, 18.5, 10 | C1, C3, C4, C14, C15 | H1, H4, H14, H16a, H17 | 39.7 | 1.68 | dd, 14, 3.5 | H1, H4, H14, H16a, H17 |
| | | 2.45 | dd, 18.5, 6.5 | C1, C3, C4, C14, C15 | H1, H16a, H17 | | 2.07 | dt, 14, 3.5 | H1, H16a, H17 |
| 3 | 173.8 | | | | | 65.1 | 4.45 | m | H2a, H2b, H4 |
| 4 | 95.5 | | | | | 49.7 | 3.01 | dd, 5.5, 4.5 | H2a, H3, H14 |
| 5 | 46.0 | 4.35 | d, 6 | C1, C3, C4, C6, C14, C18 | H7, H11, H14 | 47.4 | 4.19 | br t, 6 | H4, H7, H11, H14 |
| 6 | 210.5 | | | | | 211.0 | | | |
| 7 | 68.3 | 3.32 | d, 9 | C6, C8, C11, C12, C19 | H5, H19a, H11, H19 | 69.0 | 3.75 | d, 9 | H5, H19a, H11, H19 |
| 8 | 78.3 | | | | | 78.7 | | | |
| 9 | 46.2 | 1.84 | dd, 15.5, 7 | C19 | H7, H9b, H10, H19 | 46.5 | 1.91 | dd, 15.5, 7 | H7, H9b, H10, H19 |
| | | 2.28 | d, 15.5 | C6, C7, C8, C10, C11 | H9a, H10, H19 | | 2.39 | d, 15.5 | H9a, H10, H19 |
| 10 | 79.3 | 5.05 | t, 7 | C7, C8, C20 | H9a, H9b, H11 | 79.4 | 5.10 | t, 7 | H9a, H11 |
| 11 | 41.8 | 4.21 | m | C7, C8, C9, C12, C13, C20 | H7, H10 | 42.2 | 4.22 | m | H7, H10 |
| 12 | 131.8 | | | | | 131.5 | | | |
| 13 | 135.2 | 6.54 | br s | C1, C5, C20 | H1, H14, H16a, H17 | 135.8 | 6.63 | br s | H1, H4, H14, H16a, H17 |
| 14 | 40.1 | 2.89 | m | C1, C5, C6, C12, C13 | H2, H5, H13, H16a, H17 | 42.1 | 2.86 | m | H2a, H5, H13, H16a, H17 |
| 15 | 143.0 | | | | | 145.2 | | | |
| 16 | 115.6 | 4.86 | br s | C1, C5, C20 | H1, H2, H13, H14 | 114.7 | 4.89 | br s | H1, H2, H13, H14 |
| | | 4.95 | br s | C1, C15, C17 | H17 | | 5.00 | br s | H17 |
| 17 | 18.1 | 1.66 | s, 3H | C1, C15, C16 | H1, H2, H13, H14, H16b | 19.0 | 1.73 | s, 3H | H1, H2, H13, H14, H16b |
| 18 | 170.8 | | | | | 170.0 | | | |
| 19 | 26.6 | 1.42 | s, 3H | C7, C8, C9 | H7, H9a, H9b | 26.6 | 1.57 | s, 3H | H7, H9a, H9b |
| 20 | 169.8 | | | | | 169.5 | | | |
| 21 | 51.2 | 3.71 | s, 3H | C18 | | 52.6 | 3.78 | s, 3H | H1, H3 |
| 3-OH | | 12.15 | br s | | | | 5.38 | br d, H | |

$^1H$-$^{13}C$ correlations were determined by HMQC.

FIG. 1

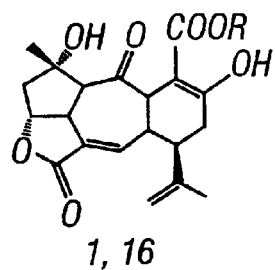
1, 16
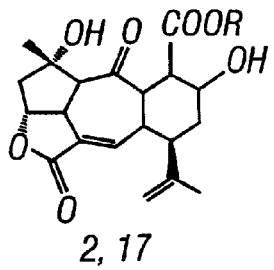
2, 17
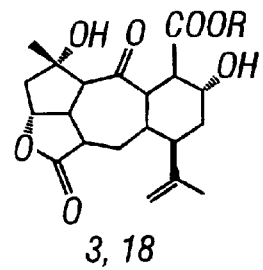
3, 18
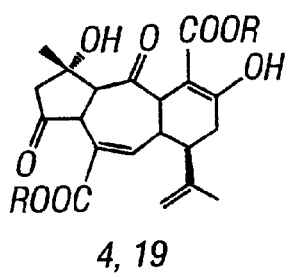
4, 19
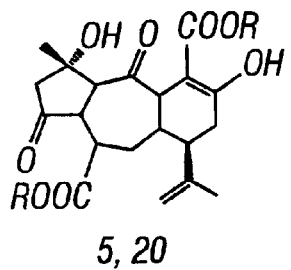
5, 20
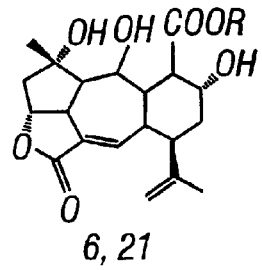
6, 21
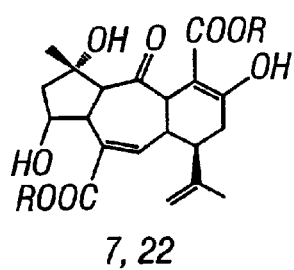
7, 22
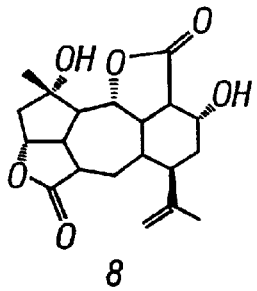
8
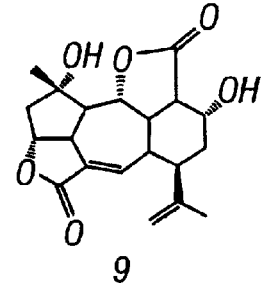
9
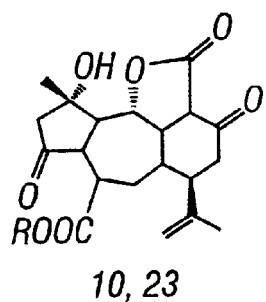
10, 23
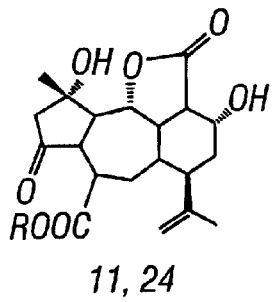
11, 24
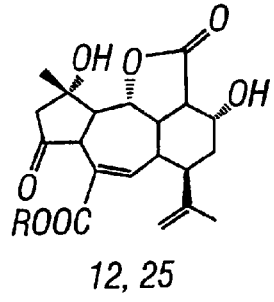
12, 25
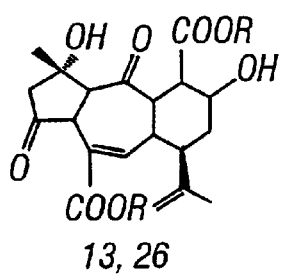
13, 26
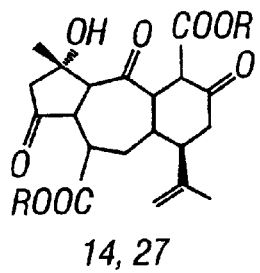
14, 27
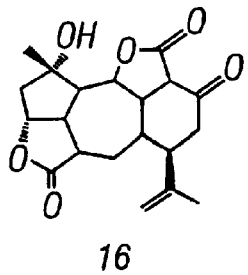
16
1-7 and 10-14  R = Me  Rameswaralide and derivatives
16-27           R = H
FIG. 2

RAMESWARALIDE AND RAMESWARALIDE DERIVATIVES

This application claims the benefit of priority of application Ser. No. 60/107,461, filed Nov. 5, 1998.

TECHNICAL FIELD

This invention relates to a chemical compound, and more particularly to diterpene derivative, rameswaralide, derived from coral.

BACKGROUND OF THE INVENTION

Inflammatory disorders are a leading cause of mortality and morbidity in the United States and affect people worldwide. Steroids and non-steroidal anti-inflammatory drugs (NSAIDs) are the most widely used therapeutic modalities. Steroids have been associated with a number of additional disorders associated with long term use, such as liver dysfunction.

Soft corals are a rich source of terpenoids with diverse structures and various biological activities. Prior studies have shown that members of the genus Sinularia produce unusual sesquiterpenes, cembrane diterpenes and sterols.

SUMMARY OF THE INVENTION

It has been discovered that rameswaralide and various derivatives of rameswaralide can function as effective anti-inflammatory agents.

In a first aspect, the invention features a diterpene molecule according to the structure of formula I:

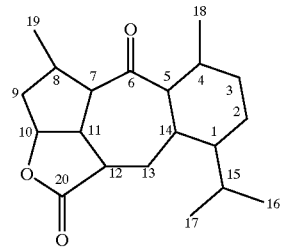

and tautomers, anhydrides, and salts thereof. In a another embodiment, the compound according to formula I has a double bond between $C_3$ and $C_4$, a double bond between $C_{12}$ and $C_{13}$, a double bond between $C_{15}$ and $C_{16}$, and wherein $C_3$ is further bonded to a $R_1$, $C_8$ is further bonded to $R_2$, and $C_{18}$ is a short chain alkoxy carbonyl and has a general structure as set forth in formula II:

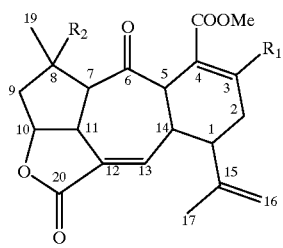

wherein $R_1$ is a hydrogen, hydroxyl group or a short chain alkanoyloxy group, and $R_2$ is a hydrogen, hydroxyl group or a short chain alkanoyloxy group.

Additionally, the diterpene molecule can have a structure as set forth in formula III:

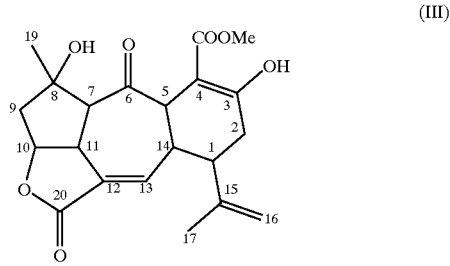

referred to herein as "rameswaralide". The diterpene molecule may be designed to be capable of traversing a biological membrane.

In one aspect, the invention features a pharmaceutical composition in unit dosage form suitable for the treatment of an inflammatory disorder. The composition consists essentially of about 40 mg to about 480 mg of the compound of formula I, II, or III (rameswaralide) or a derivative thereof. The unit dosage of the composition may be, for example, from about 175 mg to about 315 mg or from about 240 mg to about 280 mg. The composition is useful for the treatment of a wide variety of inflammatory disorders, including, for example, arthritis, psoriasis, and inflammatory bowel disease.

The invention also features an article of manufacture including packaging material and a pharmaceutical agent contained therein that is therapeutically effective for inhibiting an inflammatory disorder in a mammal. The packaging material may include a label that indicates that the pharmaceutical agent can be used for suppressing an inflammatory disorder in a mammal. The pharmaceutical agent includes rameswaralide or a derivative thereof.

In another embodiment, the present invention provides a method of obtaining the compound of formula I, II, or III. The method includes extracting the compound from coral, such as a soft coral, for example, the soft coral *Sinularia dissecta*.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 shows a table of NMR spectrum data for rameswaralide.

FIG. 2 shows derivatives of rameswaralide.

DETAILED DESCRIPTION OF THE INVENTION

The invention provides a novel diterpene compound. Thus, in a first embodiment, the present invention provides a novel compound of formula I:

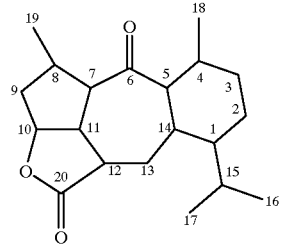

(I)

or derivatives, stereoisomer or pharmaceutically acceptable salt thereof.

In another embodiment, the structure of formula I, is modified to include a double bond between $C_3$ and $C_4$, and/or a double bond between $C_{12}$ and $C_{13}$, and/or a double bond between $C_{15}$ and $C_{16}$, $C_3$ is further bonded to $R_1$, $C_8$ is further bonded to $R_2$, and $C_{18}$ is further bonded to a short chain alkoxy carbonyl. In this embodiment the compound has the general structure as set forth in formula II:

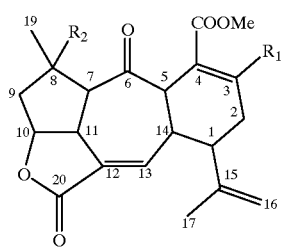

(II)

wherein $R_1$ is a hydrogen, hydroxyl group or a short chain alkanoyloxy group, and $R_2$ is a hydrogen, hydroxyl group of a short chain alkanoyloxy group. However, modifications to formula I will be apparent to those of skill in the art. For example, modification to formula I, such as a double bond between $C_4$ and $C_5$, $C_{13}$ and $C_{14}$, $C_{15}$ and $C_1$ and $C_7$ and $C_8$ are capable of being produced by one of skill in the art. Any of the above double bonds, may be further bonded (i.e., substituted) via an oxy likage (e.g., $C_3$ is further bonded to $C_4$ via an oxy linkage). Such modifications are within the skill of those in the art. Additionally, modification of the stereochemistry of the above formulas is also within the skill of those in the art. For example, the $C_8$ stereochemistry can be either R— or S—. Such stereochemical substitutions are applicable to carbons 1–20 of the present compounds so long as the compound retains its biological activity. By "biological activity" is meant the ability of the compound to inhibit, suppress or modulate inflammatory or other diseases or disorders.

Additionally, the compound has the structure of formula III:

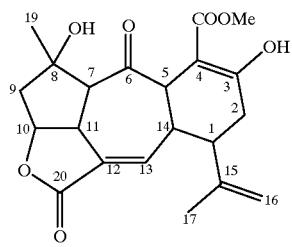

(III)

The structures of Formula I, II, or III and its derivatives are capable of forming pharmaceutically acceptable salts, including acid addition salts and base salts, as well as solvates, such as hydrates and alcoholates. All of these pharmaceutical forms are contemplated by this invention and are included herein. Acid addition salts are readily formed when a Formula I, II, or III compound contains amino substituent groups, or when nitrogen atoms are present. Base salts can be formed when carboxylic acid substituent groups are present.

Pharmaceutically acceptable acid addition salts of the compounds of Formula I, II, or III include salts derived from inorganic acids such as hydrochloric, nitric, phosphoric, sulfuric, hydrobromic, hydriodic, phosphoric, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like, gluconate, and galacturonate (see, for example, Berge S. M., et al.,"Pharmaceutical Salts," J. of Pharmaceutical Science, 1977; 66:1–19).

The acid addition salts of basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention. Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine,N-methylglucamine, and procaine (see, for example, Berge S. M., et al., "Pharmaceutical Salts," J. of Pharmaceutical Science,1977; 66:1–19).

The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in Remington's Pharmaceutical Sciences, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Prodrugs" are also encompassed by the present specification and are intended to include any covalently bonded carriers which release the active parent drug according to formula I, II, or III in vivo when such prodrug is administered to a mammalian subject, the mammal may be a human. Prodrugs of a compound of formula I, II, or III are prepared by modifying functional groups present in the compound in such a way that the modifications are cleaved, either in routine manipulation or in vivo, to the parent compound. Prodrugs include compounds of formula I, II, or III wherein a hydroxy, amino, or sulfhydryl group is bonded to any group that, when the prodrug or compound of formula I, II, or III is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula I, II, or III, and the like.

The invention provides compounds that suppress inflammatory disorders or reactions in a subject. In addition, various diterpene derivatives may be made from rameswaralide using a range of chemistries. For example, dihydrorameswaralide may be produced by selective reduction of the enolic group of rameswaralide with sodium borohydride. Additionally derivations will be recognized and are routine to those of skill in the art.

The invention also relates to a method of suppressing inflammatory responses in a subject comprising administering a compound of formula I, II or III, and particularly the compound is rameswaralide or a derivative thereof to the subject. The subject is a mammal or a human. The compounds can be administered topically, orally, intravenously, intraperitoneally, intrapleurally, intrathecally, subcutaneously, intramuscularly, intranasally, through inhalation or by suppository, depending on the type of inflammatory disorder and on various indications. For example, suppositories may be used for patients with inflammatory bowel disease. Rameswaralide or a derivative thereof may be administered in a daily amount from about 40 mg to about 480 mg. Typically the dosage ranges from about 0.5 mg/kg to about 7 mg/kg. In extreme conditions, up to about 20 mg/kg of rameswaralide or a derivative thereof may be administered. Once administered, these compounds act as anti-inflammatory agents. Without being bound by any particular theory or biochemical mechanism, these compounds may eliminate or inhibit inflammation by impeding migration of inflammatory cells including, but not limited to, monocytes, macrophages and neutrophils. Other modes of action may include inhibiting synthesis of inflammatory mediators including products of arachidonic acid metabolism, such as leukotrienes and prostaglandins.

The actual dosage of rameswaralide or derivatives thereof, formulation or composition that modulates an inflammatory disorder depends on many factors, including the size and health of an individual, however, one of one of ordinary skill in the art can use the following teachings describing the methods and techniques for determining clinical dosages (Spilker B., *Guide to Clinical Studies and Developing Protocols,* Raven Press Books, Ltd., New York, 1984, pp. 7–13, 54–60; Spilker B., *Guide to Clinical Trials,* Raven Press, Ltd., New York, 1991, pp. 93–101; Craig C., and R. Stitzel, eds., *Modern Pharmacology,* 2d ed., Little, Brown and Co., Boston, 1986, pp. 127–33; T. Speight, ed., *Avery's Drug Treatment: Principles and Practice of Clinical Pharmacology and Therapeutics,* 3d ed., Williams and Wilkins, Baltimore, 1987, pp. 50–56; R. Tallarida, R. Raffa and P. McGonigle, *Principles in General Pharmacology,* Springer-Verlag, New York, 1988, pp. 18–20) to determine the appropriate dosage to use.

In an alternative embodiment, a pharmaceutical composition containing from about 40 mg to about 480 mg of rameswaralide or a derivative thereof is provided in unit dosage form. The dose may be divided into 2–4 daily doses. Typical dosages of these pharmaceutical composition range from about 0.5 mg/kg to about 7 mg/kg. In extreme conditions, up to about 20 mg/kg may be administered. Lyophilized rameswaralide and lyophilized pharmaceutically acceptable salts are particularly useful as pharmaceutical compositions. The optimal concentration of rameswaralide or a derivative thereof in a pharmaceutically acceptable composition may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the type and extent of the inflammatory disorder, the overall health status of the particular subject and the relative biological efficacy of the compound selected. These compositions may be used for the treatment of inflammatory disorders including, but not limited to, arthritis, psoriasis, and inflammatory bowel disease. An "effective amount" or "inflammation inhibiting amount" means that amount of the compound necessary to modulate, inhibit, or suppress inflammatory responses or symptoms.

Compounds of the invention may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Sustained release compositions are also encompassed by the present invention. Compositions for other routes of administration may be prepared as desired using standard methods.

A compound of the invention may be conveniently administered in unit dosage form, and may be prepared by any of the methods well known in the pharmaceutical art, for example, as described in *Remington's Pharmaceutical Sciences* (Mack Pub. Co., Easton, Pa., 1990). Formulations for parenteral administration may contain as common excipients sterile water or saline, polyalkylene glycols such as polyethylene glycol, oils of vegetable origin, hydrogenated naphtalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as a gel to be applied intranasally. Formulations for parenteral administration may also include glycocholate for buccal administration.

The invention also relates to an article of manufacturing containing packaging material and rameswaralide or a derivative thereof contained within the packaging material. Rameswaralide or a derivative thereof are therapeutically effective for suppressing inflammation in a subject. The packaging material may contain a label or package insert indicating that rameswaralide or a derivative thereof may be used for suppressing inflammation in a subject.

In an alternate embodiment, the invention relates to compositions and kits comprising a first chemotherapeutic agent including rameswaralide or a derivative thereof and a second therapeutic agent. The second therapeutic agent is not rameswaralide or a derivative thereof. These compositions are effective to suppress inflammation in a subject. Various classes of therapeutic agents, including alkylating agents, antimetabolites, vinca alkaloids, antibiotics, cytokines, growth factors, non-steroidal anti-inflammatory drugs, such as aspirin, may be used in the composition.

Also provided are methods for obtaining the compounds of formulas I, II, or III. Such methods include chemical synthesis as well as extraction techniques. For example, rameswaralide (III) can be extracted from coral (e.g. such as the soft coral *Sinularia dissecta*). Such extraction techniques include for example, methanol extraction followed by a dichloromethanol: methanol extraction and purification on a Sephadex LH-20 column, by standard chromatography techniques. Other methods of extracting the compound from coral will be apparent to those of skill in the art. For example, modifications in column packing, elution buffers, flow rates for eluting the compound may all be modified or changed. Such modifications are routine to those of skill in the art.

The invention will be further described in the following examples, which do not limit the scope of the invention described in the claims.

EXAMPLE 1

*Sinularia dissecta* (IIC-233) was collected from the Mandapam coast near Rameswaram, Tamilnadu. The organism was soaked in methanol immediately after collection until work-up. The initial methanol was decanted and reextracted (3×1.5 L) with 1:1 diclromethane:methanol at room temperature. The combined extracts were concentrated under vacuum to obtain brownish gum.

A 1:1 dichloromethane-methanol extract of the soft coral *Sinularia dissecta* was chromatographed on Sephadex LH-20 using 1:1 dichloromethane-methanol as eluant, followed by silica gel chromatography and eluting with hexane to afford $\Delta^{9(15)}$-africanene (0.05% dry wt.), 4,5-seco-african -4,5-dione (0.0005% dry wt), β-elemene (0.0005% dry wt.), isomandapamate ((3), 0.0025% dry wt.), and a novel cembrane diterpene, rameswaralide (formula III, 0.003% dry wt.), which was purified by HPLC on silica gel using 1:3 hexane/ethylacetate as eluant. The known compounds were identified from literature data. The structure of the novel compound, rameswaralide, formula III, was determined by extensive 1D and 2D NMR experiments and confirmed by selective reduction of the enolic group with sodium borohydride to form dihydrorameswaralide, formula IV.

Rameswaralide, formula III, was obtained as a white solid, m.p. 169–171 C $(\alpha)^D$-20.5 (c=0.22, CHCl$_3$). The molecular formula $C_{21}H_{24}O_7$, which was derived from HREIMS (m/z 388.1523) and $^{13}$C NMR data, requires 10 degrees of unsaturation. The IR spectrum contained bands at 3500, 1752, 1715, 1670 cm$^{-1}$, from which the presence of a hydroxyl and three different carbonyl groups was inferred. The UV spectrum showed absorptions at 250 nm (sh, ∈11,700), 229 (sh, 15,500), 222 (15,700), 205 (14,700), which underwent reversible bathochromic shifts on addition of base, indicating the presence of an enolisable β-keto ester as well as an α,β-unsaturated carboxylic ester in the molecule. The $^{13}$C NMR spectrum (FIG. 1) contained 21 signals that include a ketone signal at δ210.5, methyl ester signals at 170.8 and 51.2, γ-lactone carbonyl signals at 169.8 and 79.3 and six olefinic carbon signals at 173.8, 143.0, 135.2, 131.8, 115.6 and 95.5. The carbonyl and olefinic carbons account for six degrees of unsaturation; hence the compound is tetracyclic. The $^1$H NMR spectrum contained signals corresponding to an isopropylidene group at δ1.66 (s, 3H), 4.86 (br s, 1H), 4.95 (br s, 1H), a conjugated trisubstituted olefinic proton at 6.54 (br s, 1H), a methine proton bearing oxygen at 5.05 (t, 1H, J=7 Hz), four low field methine protons at 4.35 (d, 1 H, J=6 Hz), 4.21 (m, 1H), 3.32 (d, 1H, J=9 Hz), 2.89 (m, 1H), a quaternary methyl at 1.42 (s, 3H) and an exchangeable proton at 12.15 ppm. The COSY spectrum revealed some similarities with mandapamate (2), which was obtained from the same specimen. The spectral data for ring A and ring C were assigned from COSY and HMBC data and the presence of allylic coupling between H-11 and H-13 established the connection between rings A and C. The chemical shifts of H-7 and H-5 and their HMBC correlations to the ketone signal at ∈210.5 completed the 7-membered ring B. An HMBC correlation between H-10 and C-20 established the presence of the y-lactone and a correlation between Me-17 and C-1 indicated that the isopropyl group was located at C-1 as expected. The fully enolized P-keto ester moiety that completes ring C was defined by the HMBC correlation from H-5 to the three carbon signals at 173.8 (C-3), 95.5 (C-4) and 170.8 (C-18) and from H-2 to C-3 and C-4. The Structure of rameswaralide, formula III, was further confirmed by selective reduction of enolic group with NaBH$_4$ to from exclusively single isomer, dihydrorameswaralide, formula IV,.

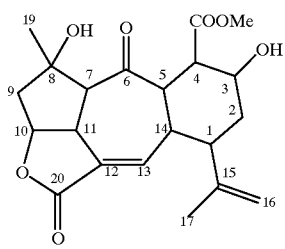

(IV)

The stereochemistry of rameswaralide, formula III, was determined by analysis of $^1$H NMR coupling constants and NOESY correlations. The coupling constants $J_{5,14}$=6 Hz and $J_{7,11}$=9 Hz and a NOESY correlation between H-5, H-7 and H-11 suggested that rings A and C are cis fused to ring B. The NOESY correlations between H-10 and H-11 and Me-19 and H-7, together with $J_{10,11}$–7 Hz, showed that Me-19, H-10, H-7 and H-11 were all on the same side of ring A. The NOESY data (FIG. 1) for dihydrorameswaralide, formula IV, showed that the H-14, H-4 and H-2a are axial and that H-5, H-3 and the isopropylidene group are equatorial with respect to ring C and also showed that rings A and B were the same as in rameswaralide, formula III.

The carbon skeleton of rameswaralide, formula III, is related to that of isomandapamate, formula V, by opening of the furan ring with a concomitant migration of the C-14 bond from C-6 to C-5.

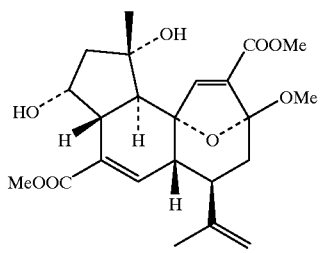

(V)

EXAMPLE 2

To provide a lypholized compound, the water solution of rameswaralide is filtered through a cotton-gauze plug or 8 layers of gauze, and a sterile Millipore filter to a sterile glass jar. The solution is vacuum pumped out of the jar into a measuring buret and aliquoted into 2 ml vials or ampules. The filled vials or ampules are maintained at −40° C. on sterile shelves for 24 hours prior to drying in a KC-30 lyophilizer or a LS-45 lyophilizer. After this tempering period, the drying process is started. The temperature is maintained at −40° C. for 2 hours, then is gradually increased to approximately 50° C. (plus or minus about 5° C.). The transition to approximately 50° C. occurs over about 12–13 hours of drying. The final temperature does not exceed +60° C. The total duration of drying time is 24 hours. After this, the vials with dry compound are immediately covered with caps.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound selected from the group consisting of formulas I, II, and III:

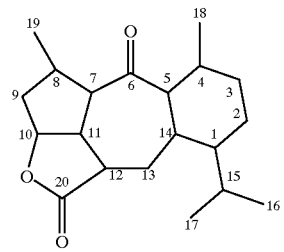

(I)

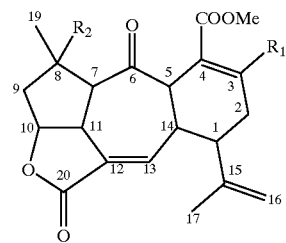

(II)

wherein $R_1$ is a hydrogen, hydroxyl group, or short chain alkanoyloxy group, and $R_2$ is a hydrogen, hydroxyl group, or short chain alkanoyloxy group

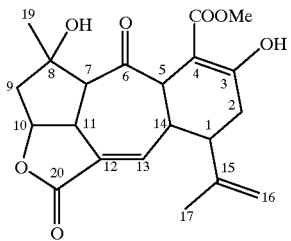

(III)

and tautomers, anhydrides, acid addition salts, base salts, solvates, and stereoisomers of compounds having structures of formulas I, II and III, compounds having the structure of formula I and having $C_3$–$C_4$, $C_4$–$C_5$, $C_7$–$C_8$, $C_{12}$–$C_{13}$, $C_{13}$–$C_{14}$, $C_{15}$–$C_{16}$, or $C_{15}$–$C_1$ double bonds or any combination thereof, compounds having the structure of formula I having $C_3$–$C_4$, $C_4$–$C_5$, $C_7$–$C_8$, $C_{12}$–$C_{13}$, $C_{13}$–$C_{14}$, $C_{15}$–$C_{16}$, or $C_{15}$–$C_1$ oxy linkages or any combination thereof, compounds having the structure of formula III having a reduced enolic group.

2. A pharmaceutical composition which comprises a compound of claim 1, combined with one or more pharmaceutically acceptable, inert or physiologically active diluents, excipients or adjuvants.

3. The pharmaceutical compostion of claim 2, wherein the composition is in unit dosage form.

4. A therapeutically active diterpene compound having the structure of formula III:

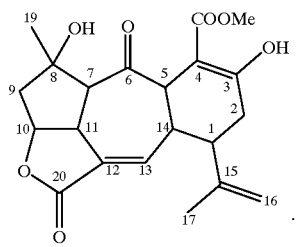

(III)

5. A therapeutic composition comprising the compound of claim 4 suitable for treating an inflammatory disorder.

6. The method of treating a mammal having an inflammatory disorder comprising administering to the subject a therapeutic composition comprising one or more pharmaceutically acceptable, inert or physiologically active diluents, excipients or adjuvants and an inflammation inhibiting effective amount of compound of claim 1.

7. The method of claim 6, wherein the subject is a mammal.

8. The method of claim 7, wherein the mammal is a human.

9. The method of claim 6, wherein the inflammatory disorder is selected from the group consisting of arthritis, psoriasis, and inflammatory bowel disease.

10. A method of obtaining a compound of claim 1, comprising, extracting the compounds from coral.

11. The method of claim 10, wherein the coral is soft coral.

12. The method of claim 11, wherein the soft coral is Singularia sp.

13. The pharmaceutical compostion of claim 2, wherein the compound comprises an inflammation inhibiting amount of the compound of formula I, and wherein the composition further comprises a pharmaceutically acceptable carrier.

14. The pharmaceutical campostion of claim 2, wherein the compound comprises an inflammation inhibiting amount of the compound of formula II, and wherein the composition further comprises a pharmaceutically acceptable carrier.

15. The pharmaceutical composition of claim 2, wherein the compound comprises an inflammation inhibiting amount of the compound of formula III, and wherein the composition further comprises a pharmaceutically acceptable carrier.

16. The method of claim 6, wherein the compound comprises the compound of formula I.

17. The method of claim 6, wherein the compound comprises the compound of formula II.

18. The method of claim 6, wherein the compound comprises the compound of formula III.

19. The method of claim 10, wherein the compound comprises the compound of formula I.

20. The method of claim 10, wherein the compound comprises the compound of formula II.

21. The method of claim 10, wherein the compound comprises the compound of formula III.

22. An article of manufacture consisting essentially of the pharmaceutical composition of claim 2 contained within packaging material, and a label or an insert containing instructions for suppressing inflammation in a mammal.

* * * * *

UNITED STATES PATENT AND TRADEMARK OFFICE
CERTIFICATE OF CORRECTION

PATENT NO.   : 6,300,371 B1
DATED        : October 9, 2001
INVENTOR(s)  : Y. Venkateswarlu, Dr. John Faulkner, K. V. Raghavan and J. S. Yadav It is certified that error appears in the above-identified patent and that said Letters Patent is hereby corrected as shown below:

Column 1,
Line 6, please add the following paragraph, as a separate paragraph:

-- <u>Statement as to Federally Sponsored Research</u>

This invention was made with Government support under Grant CA 49084 awarded by the National Institute of Health. The Government may have certain rights in this invention. --

Signed and Sealed this

Twenty-first Day of May, 2002

Attest:

JAMES E. ROGAN
*Attesting Officer*     *Director of the United States Patent and Trademark Office*